United States Patent
De Waard et al.

(10) Patent No.: US 8,147,875 B2
(45) Date of Patent: Apr. 3, 2012

(54) DERMATOLOGIC USE OF MILK PROTEINS

(75) Inventors: Rick De Waard, Nieuwegein (NL); Angela Loriann Walter, Treadwell, NY (US)

(73) Assignee: Campina Nederland Holding B.V., Zaltbommel (NL)

( * ) Notice: Subject to any disclaimer, the term of this patent is extended or adjusted under 35 U.S.C. 154(b) by 1094 days.

(21) Appl. No.: 11/908,781

(22) PCT Filed: Mar. 14, 2006

(86) PCT No.: PCT/NL2006/050055
§ 371 (c)(1),
(2), (4) Date: Dec. 5, 2007

(87) PCT Pub. No.: WO2006/098625
PCT Pub. Date: Sep. 21, 2006

(65) Prior Publication Data
US 2008/0193551 A1    Aug. 14, 2008

(30) Foreign Application Priority Data

Mar. 15, 2005 (EP) .................................. 05102043

(51) Int. Cl.
*A61K 35/20* (2006.01)
*A01N 37/18* (2006.01)
(52) U.S. Cl. .......................... 424/535; 514/859; 514/2.5
(58) Field of Classification Search .................. 424/535
See application file for complete search history.

(56) References Cited

U.S. PATENT DOCUMENTS

| | | | |
|---|---|---|---|
| 6,319,895 B1 * | 11/2001 | Tomita et al. | 514/8 |
| 2003/0190303 A1 * | 10/2003 | Kimber et al. | 424/78.05 |
| 2004/0214750 A1 | 10/2004 | Georgiades | |

FOREIGN PATENT DOCUMENTS

| | | | |
|---|---|---|---|
| EP | 0 556 083 | | 8/1993 |
| EP | 0955058 B1 | * | 11/1999 |
| EP | 2781150 | * | 1/2000 |
| JP | 7-300425 | | 11/1995 |
| WO | WO 98/44940 | | 10/1998 |

OTHER PUBLICATIONS

Adebamowo et al., "High school dietary dairy intake and teenage acne," 2005, Journal of the American Academy of Dermatology, vol. 52, 207-214.*
Dionysius et al., "Antibacterial peptides of bovine lactoferrin: Purification and characterization," *J. Dairy Science, American Dairy Science Assoc.*, vol. 80, No. 4, 1997, pp. 667-674.
International Search Report for PCT/NL2006/050055, mailed Aug. 9, 2006.
Kiratli et al., "Tear lactoferrin levels in chronic meibomitis associated with acne rosacea," *Europ. J. of Ophthal.*, vol. 10, No. 1, Jan. 2000, pp. 11-14.
Morgan-Grampian Ltd., "Milk Proteins for Cosmetics," *Manufacturing Chemist*, vol. 63, No. 1, Jan. 1992, p. 36.
Toba et al., "Milk basic protein promotes bone formation and suppresses bone resorption in healthy adult men," *Bioscience, Biotech. and Biochem.*, vol. 65, No. 6, Jun. 2001, pp. 1353-1357.
Ward et al., "Lactoferrin and Host Defense," *Biochem. and Cell Biology*, vol. 80, No. 1, 2002, pp. 95-102.

* cited by examiner

*Primary Examiner* — Ruth Davis
*Assistant Examiner* — Sheridan MacAuley
(74) *Attorney, Agent, or Firm* — Gilberto M. Villacorta; Sunit Talapatra; Foley & Lardner LLP

(57) ABSTRACT

The invention provides a method for the treatment of acne comprising orally administering to a person suffering from acne an effective amount of a whey protein fraction containing lactoferrin, and preferably containing further specific whey proteins. The lactoferrin is preferably native bovine lactoferrin and the whey protein fraction is administered at a level of between 10 mg and 2 g lactoferrin per patient per day.

13 Claims, No Drawings

DERMATOLOGIC USE OF MILK PROTEINS

PRIOR RELATED APPLICATIONS

This is a U.S. National Stage application of PCT/NL2006/050055 filed Mar. 14, 2006, which claims priority to European application 05102043.6 filed Mar. 15, 2005.

BACKGROUND

Acne

Acne vulgaris is an easily recognisable dermatologic disease. It is one of the commonest skin diseases, with a prevalence reaching nearly 100% among adolescents. Diminutive non-inflammatory acne lesions may not be more than a minor annoyance but, in persons with more harsh inflammatory nodular acne, soreness, social embarrassment, and physical as well as psychological scarring can be life-changing.

The earliest microscopic lesion observed in acne vulgaris is the microcomedo. This lesion is characterised by follicular plugging of the duct of a pilosebaceous unit (which consists of a hair follicle and a sebaceous gland). Sebum is produced in the pilosebaceous unit and some may be trapped beneath the keratin plug along with more keratinaceous material, causing enlargement of the follicle. At the microcomedo stage, follicular epithelial hyperproliferation (hyperkeratosis), follicular plugging, as well as hyperactivity of the sebaceous glands are noticeable.

The microcomedo is the precursor of other acne lesions: As the lesion increases, it becomes clinically apparent and becomes a non-inflamed closed or open comedo (whitehead or blackhead, respectively). In time the (micro)comedo may fill with *Propionibacterium acnes* bacteria, which secrete chemotactic and pro-inflammatory cell wall and biological by-products. As a consequence, inflammatory cells surround the follicle, disperse through the follicular wall, and generate enzymes that disrupt the follicular wall. In return this will lead to larger and often inflammatory lesions, such as papules, pustules, and nodular cystic lesions. Other factors, such as genetic predisposition, stress, and diet, may also affect the development and severity of acne.

Current Therapies

Topical and systemic therapies form two of the major therapeutic strategies for the treatment of acne today. Dependent on the severity of the lesions, a single or combined therapy is applied. In general, the topical and systemic therapies aim at inhibition of hyperkeratosis and follicular plugging, diminishment of sebum production, reduction of bacterial load and inflammatory responses.

The main strategies of topical therapies (in gel, cream and solution formulations) comprise topical retinoids and topical antibiotics. Systemic or oral therapies are mainly used for individuals with moderate to severe forms of inflammatory acne. For both males and females, these therapies include oral antibiotics and oral retinoids. Hormonal treatment, including oral contraceptives, is occasionally used for most types of acne in both adult and adolescent females.

However, many adverse side effects are apparent when using the therapies mentioned above, varying from dryness, redness and irritation of the skin when using retinoids, to increased antibiotic resistance when using antibiotics, and to weight gain and thrombosis when using oral contraceptives. The latter is also clearly not suitable for male individuals.

PRIOR ART

US 2004/0214750 discloses a topical anti-acne cream containing bovine lactoferrin and plant-derived components, which shows improvement in acne after administration for 10 weeks. Also, the combined administration of this topical cream with an oral product containing lactoferrin in sunflower oil is reported to result in significant improvement of skin condition. The origin and nature of the lactoferrin is not disclosed, nor is the dosage disclosed. This document insists on the importance of the topical treatment and no suggestion is made for oral administration only.

WO 98/44940 describes methods for inhibiting activity of interleukin 1β by administering lactoferrin. A wide variety of allergen-induced conditions are mentioned, such as arthritis, asthma, sinusitis, rhinitis and bronchitis, and including skin disorders, such as dermatitis, psoriasis, UV-induced inflammation, diaper rash, and wrinkles. Preferred oral dosage levels of an "active ingredients" are from 50 mg to 500 mg per kg body weight per day, which corresponds to about 3 to 40 g per adult person per day. For skin-related disorders, only topical formulations are contemplated. Experiments indicate that lactoferrin has an inhibiting effect on the synthesis of tumour necrosis factor α, which is reported to be support for an activity against allergen-induced disorders, but there is no experimental evidence of lactoferrin being active against skin disorders such as acne.

JP-A 7-300425 describes beverages and other compositions containing lacto-ferrin for the prevention of adhesion of pathogenic bacteria (e.g. *E. coli*) and cariogenic fungi. It also describes a lotion for the prevention of skin inflammation and pimples.

It is an object of the present invention to provide means and methods for the treatment of acne using natural or nature-like agents and having improved effectiveness.

DESCRIPTION OF THE INVENTION

It was found according to the invention that acne can be effectively treated by administering an oral composition containing a whey protein fraction comprising lactoferrin. Additional topical treatment is not necessary and is in fact undesired. Hence, the invention pertains to a method of treating acne, comprising orally administering to a person suffering from acne an effective amount of a whey protein fraction comprising lactoferrin.

The lactoferrin to be used in the method of the invention is preferably native bovine lactoferrin. Bovine lactoferrin is an 80-kDa iron-binding glycoprotein, which is present in exocrine secretions that are commonly exposed to normal flora: milk, tears, nasal exudate, bronchial mucus, gastrointestinal fluids, cervicovaginal mucus, seminal fluid and saliva. The usual source of bovine lactoferrin is colostrum, milk or whey. A particularly advantageous material is a whey protein fraction enriched in lactoferrin, containing between 50 and 98 wt. % of lactoferrin, more preferably between 60 and 95% of lactoferrin, the remainder being other whey proteins or peptides. Higher levels than 95% or even than 98% can also be used but were found not to give additional advantages, and on the other hand will increase cost. In particular embodiments, the lactoferrin content of the fraction is between 75 and 90 wt. %, or, alternatively, between 90 and 98 wt. %. In this respect, proteins and peptides as GMP (glycomacropeptide) and Proteose Peptones, which originate from the casein of the milk, are also called whey proteins. It is preferred that the other whey proteins are basic, i.e. they elute from an acidic ion exchange resin, and have isoelectric points above pH 6, especially above 7. It is also preferred that the other whey proteins have a molecular weight between 10 kD and 60 kD.

Preferably the whey proteins or whey peptides comprise an N-terminal sequence selected from the following group:

Ile-Gln-Arg-Pro-Pro-Lys-Ile-Gln-Val-Tyr

Xaa-Pro-Val-Thr-[Asp or Arg]-Glu-Asn-Thr-Pro-Ile (Xaa is any amino acid, in particular Gly, Ala, Arg, Met, Val, Phe, or Thr)

Xab-Lys-Glu-Thr-Asn-Tyr-Pro-Asn-Lys-Gly (Xab is Ser, Gly, or Asp).

It is noted that in the above sequences one or two of the individual amino acid residues may be exchanged by another amino acid residue, and moreover that the N-terminus may be provided with one or two additional amino acid residues.

Preferably, the whey protein fraction contains less than 5 wt. % of immunoglobulins, especially less than 2 wt. %. Furthermore, it is preferred that the fraction is low in lactoperoxidase, i.e. less than 10 wt. %, especially less than 4 wt. %. Preferably, the weight ratio between lactoperoxidase and lactoferrin is below 0.4, more in particular between 0.01 and 0.2.

The lactoferrin of the whey protein fraction preferably has an iron content of between 50 and 400 ppm of iron ($Fe^{3+}$), more preferably between 75 and 300 ppm, and most preferably between 100 and 200 ppm, based on pure lactoferrin. The iron content of the whey protein fraction as such is preferably between 40 and 350 ppm, more preferably between 60 and 250 ppm, and most preferably between 80 and 180 ppm, of the whey protein weight. The lactoferrin is preferably native, i.e. essentially non-denatured.

The lactoferrin-containing fraction may be obtained by fractionation of whey proteins using affinity chromatography, ion exchange chromatography, ultrafiltration, and the like and combinations thereof. The process generally starts from a milk product, which is usually defatted first, e.g. by microfiltration or centrifugation. The process may further comprise loading on an acid ion exchange resin, washing, eluting a basic fraction, concentrating, desalting the basic fraction and drying (e.g. spray-drying).

The source of the milk product may be human, cow, goat, sheep, lama, yak, buffalo, horse, etc. The milk product may be milk, concentrated milk, delactosed milk, pasteurised milk, thermised milk; whey, defatted whey, cheese whey, casein whey, lactic acid whey, concentrated whey, delactosed whey, ultrafiltrated or nanofiltrated whey, WPC (whey protein concentrates), and other milk fractions containing most or all of the milk proteins other than intact casein.

The ion exchange resin can be of the strong acid type (sulfonic-acid type), or of the weak acid type (carboxylic acid type). The latter is preferred. Preferred are the macroporous, synthetic polymers, e.g. based on polymethacrylate. Exemplary types include Sepabeads FP-SP from Mitsubishi (Italy) and Amberlite IRC 50 from Röhm & Haas (USA).

Although native bovine lactoferrin is a preferred component of the whey protein fraction to be used as an active agent, part (e.g. up to 50% by weight or more) or all of it may be replaced by other lactoferrins, such as lactoferrin from other mammals (humans and other primates, horses, goats, camels and others), recombinant lactoferrin (human, bovine and other) produced in animals or plants, truncated lactoferrin, lactoferrin-derived peptides (lactoferricin, lactoferrampin and other), acid-treated lactoferrin as described in the pending application PCT/EP2004/001849, and immobilised lactoferrin as referred to in WO 0072874. The lactoferrin may especially be a constituent of lactoferrin-containing fluids (whey, milk, colostrums,) or a composition comprising lactoferrin and milk-derived growth factors as described in EP 869 134 A1.

The lactoferrin and other whey proteins may be used as such or combined with other active agents or support components. Non-limiting examples of additional components that may be used are mammalian derived bioactive proteins (such as lactoperoxidase), glycoproteins, enzymes, carbohydrates, polysaccharides (e.g. pectin, carboxymethylcellulose, carrageenan, heparins) fatty acids, peptides, amino acids, growth factors, lysozyme, histatins, cystatins, casein, casein phosphopeptide (CPP), peptides or peptide mixtures enriched in one or more specific, e.g. (conditionally) essential, amino acids like glutamine, cysteine, glycine, arginine, tryptophan etc.; anti-hypertensive peptides, retinoids, vitamins and hormones; non-animal compounds, i.e. plant, recombinant, chemical or other origins, antibiotics, fibres, probiotics, prebiotics, retinoids, vitamins, hormones, bacteriocins, lactic acid, and herbs.

The lactoferrin-containing protein fraction may be formulated in a way which is conventional for oral pharmaceutical or nutritional compositions. Where the composition to be administered is a nutritional composition, it may be as a food supplement, bar, drink, yoghurt, sweet, gum, etc. Such food products contain at least one of carbohydrates and non-whey proteins, such as casein, optionally together with further food components, such as fats, fibres, vitamins, minerals, and optional additives such as flavours, sweeteners, stabilisers and the like. Preferably the weight ratio between lactoferrin-containing whey protein fraction and the carbohydrate and/or non-whey protein is between 1:4 and 1:100, more preferably between 1:9 and 1:49.

Where the composition is a pharmaceutical composition, it may e.g. be a tablet, granule, powder, syrup, capsule, solution, gel, lozenge, etc., containing conventional excipients, such as water, starch, starch derivatives (e.g. sodium starch glycolate) or starch fractions, microcrystalline cellulose or cellulose derivatives, pectin, other poly-saccharides, lactose, other sugars, etc. Tablets, especially chewable tablets, constitute a preferred embodiment of the pharmaceutical composition of the invention, since absorption through the oral mucosa avoiding the gastro-intestinal tract is believed to be an additional advantage. A chewable tablet is preferably soft and preferably has a total weight of at least 750 mg per unit. It is preferred that in tablets the content of (reducing) sugars is relatively low (e.g. less than 25 wt. %, especially less than 10 wt. % of the dry tablet matter), and that the excipients are selected from e.g. non-reducing sugars, polysaccharides and sugar alcohols for at least 50 wt. %, or even at least 70 wt. % of the composition. Solids dosage forms may also be coated with an enteric coating. Although other systemic administration routes may be suitable, such as rectal, nasal or parenteral routes, the preferred administration route is orally.

The dosage level will depend on various individual factors, such as age, physical and nutritional condition, severity of acne, which can be assessed by the technician or physician. Typical dosage levels will be in the range of between 10 mg and 2 g whey protein fraction comprising lactoferrin per patient per day, preferably between 20 mg and 1.2 g. For an effective treatment, dosages of at least 40 mg or preferably at least 60 mg or even at least 80 mg per day are preferred, e.g.

between 40 and 800 mg or up to 600 mg lactoferrin per patient per day. In terms of body weight, the dosage levels are generally between 0.1 and 50 mg lactoferrin per kg per day, preferably between 0.25 and 25 mg, more preferably between 0.5 and 15 mg/kg.day, or even between 1 and 10 mg/kg.day.

The daily dosages may be administered in a single dosage unit or, preferably, over multiple daily dosages, e.g. 2-4 times a day. Thus, in case a single dosage unit (e.g. a tablet) is used daily, the dosage unit contains at least 10 mg, but preferably at least 40 mg lactoferrin per unit. In case of two dosage units per day, the dosage unit contains at least 10, but preferably at least 20 mg and even more preferably at least 30 mg per unit. Using more frequent daily dosages, the amount of lactoferrin per unit is similarly such that the total daily amount is preferably at least 40 mg, preferably at least 80 mg.

The treatment can be continued for a period ranging from several days to several months, e.g. between 1 week and 6 months, or even longer if necessary. The dosage levels can be kept constant over the treatment period. Alternatively, and advantageously, the treatment can start at relatively high dosages, e.g. between the levels indicated above and twice these levels for a first period of e.g. between 1 and 6 weeks, followed by relatively low dosages of e.g. half the levels indicated above, for a second period of e.g. between 4 weeks and 1 year or even longer. The treatment can be given to any subject suffering or liable to suffering from acne. In cases of severe acne which, without treatment, tends to increase even further in time, the treatment can also be given as a means to inhibit further expansion of acne. The anti-acne treatment can also suitably be given during the menstrual period.

The invention also pertains to a lactoferrin-containing composition, further containing between 2 and 25 wt. %—on total protein basis—of basic proteins having a molar weight between 10 and 60 kD, as described above. The invention furthermore relates to an oral dosage unit containing at least 10 mg of lactoferrin or higher amounts referred to above depending on the administration mode (single or multiple daily dosage). The dosage unit can be a pharmaceutical composition (e.g. a tablet) or a nutritional composition as detailed above.

EXAMPLES

Example I

Preparation of Whey Protein Fraction Containing Lactoferrin

Cheddar whey was thermized at 60° C. for 20 seconds, and was concentrated 3-5 times using reverse osmosis. The concentration step was done at a maximum temperature of 30° C. at pH 6.2. The concentrated whey was passed over a column loaded with an acid ion exchange resin of the type Amberlite IRC-50. Loading of the column was carried out at 6-8 bed volumes per hour, and less than 20 bed volumes per cycle. Under these conditions, up to about 2 grams of lactoferrin binds per litre of ion exchange resin. Subsequently, the resin was washed with at least 4 bed volumes of water, followed by washing with a salt solution of less than 0.5 M NaCl. The desired fraction was eluted using 1 M of NaCl or more. It was not necessary to include a buffer in the elution buffer. The eluted fraction was desalted and concentrated using ultra-filtration/diafiltration as is known in the art. Next, the concentrate was microfiltered, and spray-dried. Analysis of the product was done using by running a PAGE gel electrophoresis (20% acrylamide) and Western blotting the gel on a PVFD membrane. Subsequently the major bands were cut out and subjected to an automated sequential Edman degradation method to determine the first 10 N-terminal amino acids of the peptide or protein.

Example II

Tablets Containing the Composition Obtained in Example I

The following ingredients were used to produce tablets containing 50 mg lactoferrin

| Ingredient | mg per tablet |
|---|---|
| Sorbitol P60W | 700 |
| Mannitol DS200 | 200 |
| Primojel (sodium starch glycolate; DMV International) | 40 |
| Product of Example I (79.6% lactoferrin) | 62.8 |
| Malic acid | 6 |
| Mg stearate (Witco Regular) | 5 |
| Orange Flavor (Natural) Ottens S-627 | 3.2 |
| Orange Color FD&C Yellow #6, alum lake 35-42% | 1.4 |
| Total | 1018.4 |

Preparation of Tablets:

All ingredients minus the Mg stearate were mixed for 10 minutes. Then the stearate was added and mixing continued for 3 minutes. Chewable tablets of size ⅝ were made by direct compression.

Example III

In Vivo Study of the Effect of Whey Protein Fraction on the Control of Acne

Forty-four teenagers were enrolled into the study (23 males and 21 females, with an average age of 15.3 years (range 13 to 19)). The subjects took four chewable tablets containing bovine whey protein fraction containing lactoferrin (prepared according to example 1) at 251 mg of whey protein fraction per day (200 mg lactoferrin per day) for 12 successive weeks, consumed as two tablets in the morning and two in the evening. Subjects had front profile photographs taken and evaluated by a dermatologist. Subject data were collected at week 1, which occurred before treatment started, as well as at weeks 2, 4, 8 and 12. The study was designed for 12 weeks, photographs were evaluated through week 8 and teenagers were interviewed at week 12. The numbers of blackheads (open comedones) and non-blackheads (including whiteheads (closed comedones), papules, pustules and nodulocystic lesions) were counted on the forehead, left cheek, right cheek, chin, and nose. Blackheads and non-blackheads were summed over the facial regions for each subject at each week. The results are given in table 1 below. All of these sequential differences were highly significant (P<0.001 in all cases).

In the interviews at week 12, 80% of the teenagers reported improvements, i.e. reduced acne, and wished to continue the therapy. Over 90% of the teen-age study population would recommend the therapy to others suffering from acne. Furthermore, the teenagers also reported additional beneficial effects. They felt healthier and were less sick or not sick at all (in comparison to family members or friends which did not take lactoferrin).

TABLE 1

Counts of blackheads, non-blackheads (including whiteheads (closed comedones), papules, pustules and nodulocystic lesions), and total blemishes (blackheads + non-blackheads), by week.

| Result | Week | Mean (standard deviation) | Minimum | Median | Maximum |
|---|---|---|---|---|---|
| Blackheads | 1 | 56 (72) | 0 | 33 | 404 |
|  | 2 | 25 (43) | 0 | 12 | 267 |
|  | 4 | 18 (32) | 0 | 9 | 194 |
|  | 8 | 4 (7) | 0 | 1 | 27 |
| Non-blackheads | 1 | 16 (18) | 0 | 8 | 77 |
|  | 2 | 8 (8) | 0 | 5 | 35 |
|  | 4 | 5 (5) | 0 | 2 | 21 |
|  | 8 | 1 (3) | 0 | 0 | 12 |
| Total Blemishes | 1 | 71 (81) | 2 | 44 | 452 |
|  | 2 | 33 (48) | 1 | 18 | 302 |
|  | 4 | 22 (34) | 0 | 11 | 207 |
|  | 8 | 5 (8) | 0 | 1 | 30 |

The data obtained from the study with teenagers demonstrate that orally administrated bovine lactoferrin is able to substantively reduce acne vulgaris. Using regression models, no evidence was found that the changes over time were affected by gender or age. This implies that males and females followed similar longitudinal patterns, as did subjects through the entire age range of 13 to 19 years. No adverse side effects were reported. The majority of the study population testified beneficial effects of intake of the whey protein fraction. They noticed reduced acne, felt better and healthier, and were determined to continue ingestion of the tablets.

Altogether, the outcome of the study forms a solid base to position natural, bovine milk-derived bioactive whey composition comprising lactoferrin intake as a new strategy to prevent and treat acne vulgaris. In contrast to current systemic and topical therapies (based on antibiotics, retinoids and other compounds), lactoferrin/whey composition supplementation is not accompanied by side effects and can be used on an enduring basis.

Example IV

In Vivo Study of Different Administration Forms of Lactoferrin on Acne

Chewable tablets A and B (containing 6.25 and 25 mg of lactoferrin per tablet, respectively) were prepared using the amounts as given in the table below (amounts in mg per tablet). The tablets were prepared as described in example I.

|  | A (6.25 mg) | B (25 mg) |
|---|---|---|
| Sorbitol P60W | 756.7 | 732.4 |
| Mannitol SD200 | 200 | 200 |
| Sodium starch glycolate | 40 | 40 |
| Lactoferrin product; 77.2% lactoferrin | 8.1 | 32.4 |
| Malic acid | 6.0 | 6.0 |
| Magnesium stearate (Witco regular) | 5.0 | 5.0 |
| Orange flavour (natural) (Ottens S-627) | 3.2 | 3.2 |
| Orange colour D&C Yellow #6, Alum lake 35-42% | 1.4 | 1.4 |
| Total weight | 1020.4 | 1020.4 |

A topical cream C was prepared from the following ingredients (amounts in g).

|  | C |
|---|---|
| Phase 1 |  |
| Tefose 63 Non-ionic emulsifier: (PEG-6 Stearate, glycol stearate, & PEG-32 stearate) | 200.0 |
| Labrafil M 1944 CS (Oleoyl macrogol-6 glycerides) | 30.0 |
| Mineral Oil | 30.0 |
| De-ionised water (sterile-filtered) | 616.9 |
| Phosphoric Acid 80% | 1.6 |
| Phase 2 |  |
| Lactoferrin (77.2% lactoferrin), 15% solution in water | 121.5 |
| Total weight | 1000.0 |

Phase 1 was mixed and heated to 75° C. The mixture was then slowly cooled while stirring. Phase 2 was added at 50° C. The resulting mixture was divided in tubes of 30 g each, containing 14.2 mg lactoferrin per g.

Forty (40) subjects, ages 12-19, female and male, meeting the following criteria:

Mild to moderate acne;

Not currently taking oral prescription or OTC medication for the treatment of acne;

Not having a chronic disease with facial skin manifestations;

Not treated with antibiotics within 1 month prior to the study;

Not pregnant, lactating or intending to become pregnant;

Not having a known allergy to cow's milk or milk products; were divided in three groups:

Group 1 (N=14; 9 males, 5 females; average age 15.0 years; average acne duration 3.9 years): Subjects received lactoferrin-containing tablets A with a recommended consumption of 2 tablets in the morning and 2 in the evening corresponding to 25 mg lactoferrin per day for 6 weeks.

Group 2 (N=14; 7 males, 7 females; average age 15.1 years; average acne duration 3.8 years): Subjects received lactoferrin-containing tablets B with a recommended consumption of 2 tablets in the morning and 2 in the evening corresponding to 100 mg lactoferrin per day for 6 weeks.

Group 3 (N=12; 6 males, 6 females; average age 15.2 years; average acne duration 3.6 years): Subjects received lactoferrin-containing tablets A with a recommended consumption of 2 tablets in the morning and 2 in the evening corresponding to 25 mg lactoferrin per day plus topical lactoferrin cream C to be topically applied at 2.45 ml per day.

At T=0, photographs were taken of front profiles of the subjects and scored by an independent dermatologist and a review of inflamed and blemished areas on the face was conducted. Subjects received the tablets or tablets and cream, with instructions for use, as well as questionnaires for documenting their experiences during the study, including burning and itching feelings.

At 2, 4 and 6 weeks thereafter, subjects were photographed and reviewed again, and their completed questionnaires were collected.

Because of possible seasonal effects, only relative results can be evaluated.

The results are summarised in tables 2 and 3 below:

TABLE 2

Total dermatological evaluation of acne (comedones, papules, postules, nodules and cysts) after 2 weeks and median of total evaluation (mean values), and non-inflammatory phenomena (comedones) after 6 weeks of treatment (median values).

|  | Δ 2-0 total mean (%) | Δ 6-0 median non-inflamm.(%) |
|---|---|---|
| Group 1 (oral 25) | +21 | +12 |
| Group 2 (oral 100) | −12 | −10 |
| Group 3 (oral 25 + topical) | +19 | +7 |

TABLE 3

Dermatological evaluation of open comedones, closed comedones and subjectives scores of itching after 6 weeks of treatment (median values).

|  | Change in open comedones (%) | Change in closed comedones (%) | Change in itching (%) |
|---|---|---|---|
| Group 1 (oral 25) | +14 | −16 | +50 |
| Group 2 (oral 100) | −36 | −37 | 0 |
| Group 3 (oral 25 + topical) | +35 | −27 | +67 |

The results show that oral treatment with 25 mg lactoferrin per day does not give an appreciable total effect, and gives a moderately favourable effect on closed comedones, no account being taken of seasonal effects. Additional topical treatment with 35 mg lactoferrin per day does not improve the effect, and may in fact be counterproductive, especially in the effect on open comedones and itching. Oral treatment at 100 mg lactoferrin per day, however, has a strongly improved effect, in particular on non-inflammatory phenomena (open and closed comedones).

The invention claimed is:

1. A method for the treatment of acne consisting of orally administering to a person suffering from acne a composition comprising between 40 and 800 mg per day of a whey protein fraction comprising between 50 and 98 wt. % lactoferrin for a treatment period between 1 and 6 weeks, without topical administration of lactoferrin during the treatment period.

2. The method according to claim 1, in which the whey protein fraction further comprises basic proteins or peptides having a molecular weight between 10 kD and 60 kD.

3. The method according to claim 1, in which the whey protein fraction is at a dosage level of between 40 mg and 2 g lactoferrin per patient per day.

4. The method according to claim 3, in which the whey protein fraction is at a dosage level of between 60 and 800 mg per patient per day.

5. The method according to claim 1, in which the composition further comprises a carbohydrate, a non-whey protein, or both.

6. The method according to claim 1, in which the composition is in the form of a tablet.

7. The method according to claim 6, in which the whey protein fraction comprises at least 10 mg of lactoferrin per tablet.

8. The method according to claim 6, in which the whey protein fraction comprises at least 20 mg of lactoferrin per tablet.

9. The method according to claim 1, further comprising carbohydrate and/or non-whey protein, the weight ratio between the lactoferrin-containing whey protein fraction and the carbohydrate and/or non-whey protein being between 1:4 and 1:100.

10. A method for treatment of acne comprising orally administering to a person suffering from acne between 40 and 800 mg per day of a whey protein fraction comprising between 50 and 98 wt. % lactoferrin, without topical administration of a treatment for the acne for duration of the treatment.

11. The method according of claim 10, in which between 60 and 800 mg of the whey protein fraction is administered per day.

12. The method according of claim 10, in which the whey protein fraction is administered as a tablet.

13. The method according of claim 10, in which the whey protein fraction is contained in a food or beverage comprising a carbohydrate, a non-whey protein, or both.

* * * * *